(12) United States Patent
Hegazi et al.

(10) Patent No.: US 11,662,288 B2
(45) Date of Patent: May 30, 2023

(54) METHOD FOR MEASURING API GRAVITY OF PETROLEUM CRUDE OILS USING ANGLE-RESOLVED FLUORESCENCE SPECTRA

(71) Applicant: Saudi Arabian Oil Company, Dhahran (SA)

(72) Inventors: Ezzat Hegazi, Windsor (CA); Vincent Cunningham, Ferbane (IE)

(73) Assignee: Saudi Arabian Oil Company, Dhahran (SA)

( * ) Notice: Subject to any disclaimer, the term of this patent is extended or adjusted under 35 U.S.C. 154(b) by 343 days.

(21) Appl. No.: 17/031,386

(22) Filed: Sep. 24, 2020

(65) Prior Publication Data

US 2022/0091003 A1 Mar. 24, 2022

(51) Int. Cl.
*G01N 21/64* (2006.01)
*G01N 9/24* (2006.01)
*H01L 29/765* (2006.01)

(52) U.S. Cl.
CPC ............. *G01N 9/24* (2013.01); *G01N 21/64* (2013.01); *H01L 29/765* (2013.01)

(58) Field of Classification Search
CPC ........ G01N 9/24; G01N 21/64; G01N 33/241; G01N 33/28; G01N 2021/6417;
(Continued)

(56) References Cited

U.S. PATENT DOCUMENTS

| 4,814,614 A | 3/1989 | Tsui |
| 5,049,738 A | 9/1991 | Gergely et al. |

(Continued)

FOREIGN PATENT DOCUMENTS

| AU | 2007309735 | 5/2008 |
| CA | 2758971 | 10/2010 |

(Continued)

OTHER PUBLICATIONS

Nandakumar et al., "Method of Detecting API Gravity of Oil Present in Hydrocarbon Bearing Fluid Inclusions," Indian Patent Application No. 1559/CHE/2015, Filed Mar. 26, 2015, 24 pages.
(Continued)

*Primary Examiner* — Abdullahi Nur
(74) *Attorney, Agent, or Firm* — Fish & Richardson P.C.

(57) ABSTRACT

Systems and methods include a fluorescence measurement apparatus. A single-wavelength light source generates an excitation light source. A sample holder holds a sample and includes a surface transparent to the excitation light source. Mounts attached to the single-wavelength light source(s) or the sample holder change an incident angle of the excitation light source on the surface. Optical components positioned in a path of a fluorescence emission emitted from the surface guide the fluorescence emission to a detector that obtains spectra from at least first and second angles-of-incidence. A device records spectra obtained by the detector from the first and second angles-of-incidence, normalizes and analyzes intensities of the spectra, subtracts a first spectrum corresponding to the first angle-of-incidence from a second spectrum corresponding to the second angle-of-incidence to obtain a difference, identifying a sample type of the sample based on an API gravity mapped to the difference.

20 Claims, 8 Drawing Sheets

(58) Field of Classification Search
CPC ... G01N 2021/6423; G01N 2021/6465; G01N 21/643; G01N 21/6402; G01N 33/2823; G01J 3/4406; H01L 29/765
See application file for complete search history.

(56) References Cited

U.S. PATENT DOCUMENTS

| | | | |
|---|---|---|---|
| 5,780,850 | A | 7/1998 | Delaune |
| 6,633,043 | B2 | 10/2003 | Hegazi et al. |
| 7,084,392 | B2 | 8/2006 | DiFoggio et al. |
| 7,202,947 | B2 | 4/2007 | Liu et al. |
| 8,455,845 | B2 | 6/2013 | Hegazi et al. |
| 8,980,179 | B2 | 3/2015 | Geddes |
| 9,081,175 | B2 | 7/2015 | Yang |
| 9,222,929 | B2 | 12/2015 | Chakrabarty et al. |
| 9,284,227 | B2 | 3/2016 | Niccolls et al. |
| 9,429,556 | B2 | 8/2016 | Koseoglu |
| 10,018,748 | B2 | 7/2018 | Black et al. |
| 10,371,633 | B2 | 8/2019 | Hegazi et al. |
| 10,527,546 | B2 | 1/2020 | Koseoglu et al. |
| 2003/0141459 | A1 | 7/2003 | Hegazi et al. |
| 2004/0104355 | A1 | 6/2004 | DiFoggio et al. |
| 2004/0218176 | A1 | 11/2004 | Shammal |
| 2010/0044673 | A1 | 2/2010 | Tsukada |
| 2014/0190254 | A1 | 7/2014 | Bouyer |
| 2014/0208826 | A1 | 7/2014 | Larter et al. |
| 2014/0291551 | A1 | 10/2014 | Rengifo et al. |
| 2014/0367098 | A1 | 12/2014 | Likhanova et al. |
| 2016/0084815 | A1 | 3/2016 | Rengifo et al. |
| 2016/0108687 | A1 | 4/2016 | Rapoport |
| 2016/0195508 | A1 | 7/2016 | Al-Hajji et al. |
| 2016/0238526 | A1 | 8/2016 | Fadaei et al. |
| 2016/0363533 | A1 | 12/2016 | Koseoglu et al. |
| 2017/0299516 | A1 | 10/2017 | Hegazi et al. |
| 2017/0322133 | A1* | 11/2017 | Trainer ................ G01N 21/474 |
| 2019/0128809 | A1 | 5/2019 | Hegazi et al. |
| 2020/0025665 | A1* | 1/2020 | Trainer .............. G01N 15/0205 |

FOREIGN PATENT DOCUMENTS

| | | |
|---|---|---|
| CA | 2722497 | 6/2011 |
| CA | 2844832 | 2/2013 |
| CA | 2916490 | 2/2013 |
| CA | 2899348 | 10/2015 |
| CA | 2909029 | 12/2015 |
| CA | 2940007 | 10/2016 |
| CA | 2952035 | 2/2017 |
| CA | 2952398 | 2/2017 |
| CN | 102448720 | 5/2012 |
| CN | 104837953 | 8/2015 |
| EP | 2320026 | 5/2011 |
| EP | 2419271 | 2/2012 |
| GB | 2454071 | 4/2009 |
| IN | 200561 | 5/2006 |
| IN | 200404108 P1 | 4/2009 |
| JP | H05-960052 | 3/1993 |
| JP | 2013138720 | 7/2013 |
| KR | 2012007052 | 1/2012 |
| WO | WO 2005017316 | 2/2005 |
| WO | WO 2008051299 | 5/2008 |
| WO | WO 2010121143 | 10/2010 |
| WO | WO 2011071651 | 6/2011 |
| WO | WO 2010010751 | 1/2012 |
| WO | WO 2016201254 | 12/2012 |
| WO | WO 2013023299 | 2/2013 |
| WO | WO 2013074761 | 5/2013 |
| WO | WO 2014190000 | 11/2014 |
| WO | WO 2016111997 | 7/2016 |

OTHER PUBLICATIONS

Patra et al., "Effect of sample geometry on synchronous fluorimetric analysis of petrol, diesel, kerosene and their mixtures at higher concentration," The Analyst, 2000, 125:1383-1386.

Hegazi et al., "Estimation of crude oil grade using time-resolved fluorescence spectra," Talanta, Apr. 2002, 56(6):989-995, 7 pages.

PCT International Search Report and Written Opinion in International Appln. No. PCT/US2021//051507, dated Dec. 10, 2021, 20 pages.

* cited by examiner

METHOD FOR MEASURING API GRAVITY OF PETROLEUM CRUDE OILS USING ANGLE-RESOLVED FLUORESCENCE SPECTRA

BACKGROUND

The present disclosure applies to fluid fluorescence.

Some fluids can fluoresce, that is, they give off light when stimulated by a certain wavelength of light from an external source. Different fluids are sensitive to different wavelengths of light, and different fluids fluoresce to different wavelengths of light when stimulated or excited.

X-ray fluorescence techniques can depend on an angle-of-incidence, making the techniques different from laser-induced fluorescence techniques. There is a difference between the laser angle-of-incidence and the laser angle-of-polarization.

SUMMARY

The present disclosure describes techniques that can be used for using a different in laser-induced fluorescence spectra to identify an American Petroleum Institute (API) gravity of the crude oil. In some implementations, a fluorescence-measurement apparatus includes the following. A single-wavelength light source is configured to generate an excitation light source. A sample holder defining an inner cavity is configured to hold a sample and includes a surface transparent to the excitation light source. One or more mounts attached to at least one of the single-wavelength light source or the sample holder is configured to change an incident angle of the excitation light source on the surface. One or more optical components positioned in a path of a fluorescence emission emitted from the surface is configured to guide the fluorescence emission to a detector configured to obtain spectra from at least a first angle-of-incidence and a second angle-of-incidence. A recording/analyzing device is configured to: record spectra obtained by the detector from the first angle-of-incidence and the second angle-of-incidence, normalize and analyze intensities of the spectra, subtract a first spectrum corresponding to the first angle-of-incidence from a second spectrum corresponding to the second angle-of-incidence to obtain a difference in the spectra, and identify a sample type of the sample based on an API gravity that is mapped to the difference.

The previously-described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/ the instructions stored on the non-transitory, computer-readable medium.

The subject matter described in this specification can be implemented in particular implementations, so as to realize one or more of the following advantages. First, the API gravity of crude oils can be estimated almost instantaneously by measuring the fluorescence spectra at two laser angles-of-incidence, normalizing the resulting spectra, subtracting them, and measuring the areas-under-the-curve in a particular spectral range. Second, laser-based techniques can be used when constructing a compact device. Third, a new geometrical configuration can be used in the laser-induced fluorescence of crude oils. Fourth, techniques can be used to distinguish between different crude oil samples and measure their API gravity value instantaneously.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
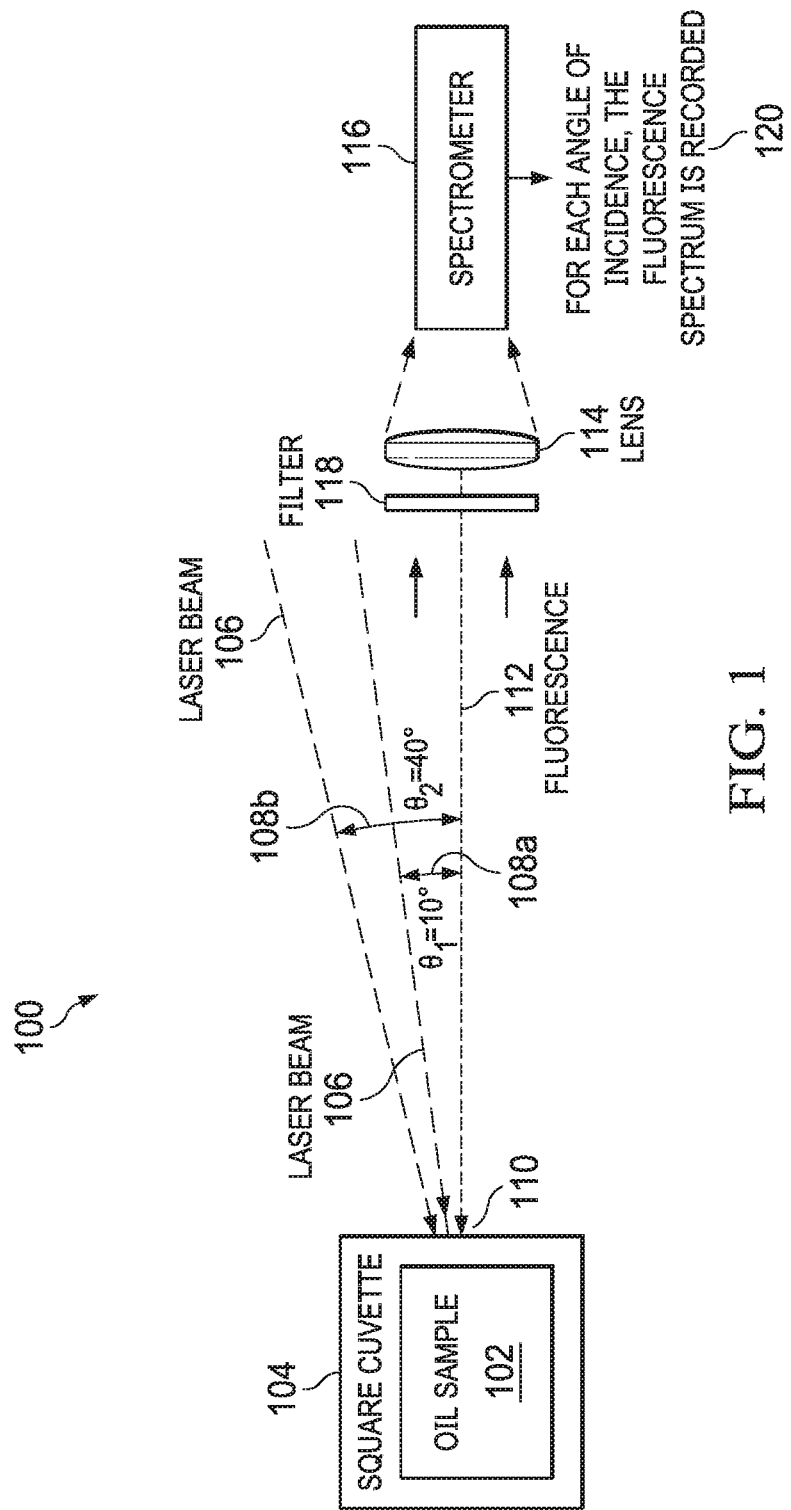
FIG. 1 is a block diagram showing an example of an experimental setup, according to some implementations of the present disclosure.

The following detailed description describes techniques for using a different in laser-induced fluorescence spectra to identify an American Petroleum Institute (API) gravity of the crude oil. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The techniques of the present disclosure can include a process for performing API gravity characterization of petroleum crude oils using angle-resolved, laser-induced, fluorescence measurements. The process includes measuring the wavelength-resolved, fluorescence spectra from oil when an excitation laser beam hits an oil sample from two different angles. The measured spectra can then be normalized relative to intensity at a particular wavelength, subtracted from each other, and their areas under the curve can be calculated. Experience can show that the areas under the curve in a specific wavelength range correlate linearly to the API gravity of the crude oil. As a result, a standard calibration can be constructed to determine the API gravity of unknown crude oils.

Attributes of the present disclosure include the following. Techniques can be used for instantly measuring the API gravity of crude oils by exciting the laser-induced fluorescence of oils at two different angles-of-incidence. The techniques include non-destructive techniques which do not require the preparation of a sample. The techniques can be used in the manufacture of a compact, handheld (or hand-carried) device. Measurements and calibration can be performed using a minimum amount of oil. As an example, an oil sample size can be 1-4 milliliters (ml).

The present disclosure describes techniques that can take advantage of the slight change in the penetration depth of a laser beam inside a fluorescence-capable liquid as the angle-of-incidence of the laser is changed at the liquid surface. In particular, the wavelength of the laser beam must be one that can induce a fluorescence emission in the liquid. As the excitation laser beam penetrates inside the liquid, the beam gives rise to a primary fluorescence emission due to the original photon energy of the laser. In addition, a secondary emission is created inside the liquid. The secondary emission originates from the continuous absorption-reemission processes that occur between the deeper layers of the liquid. This effect is sometimes referred to as an inner filter effect for the liquid. In other words, the already-emitting deeper layers act as additional secondary light sources to their adjacent layers, inducing an extra fluorescence emission contribution. The overall effect on the fluorescence emission from this additional lower energy contribution is translated into a red shift in the fluorescence spectrum, which increases with depth.

The increase in the red shift with depth is expected for any single liquid. The extent of the red shift in the fluorescence spectrum, on the other hand, is not expected to be the same for different liquids. This is due to several factors, including the different absorption coefficients and the different fluorescence quantum yields that different liquids exhibit.

The present disclosure describes a process that correlates the red shift in the fluorescence spectra of petroleum crude oils to their API gravity. Petroleum crude oils are opaque liquids, which attenuate the impinging ultraviolet laser beam within the first 1-2 millimeters of depth. The process relies on creating different depths within such a small range by changing the laser angle-of-incidence. The process further relies on normalizing the intensities of the measured fluorescence spectra at one particular wavelength.

During experiments, four crude oil samples with different API gravities were used. The samples included Extra light (API°=39.2), Light (API°=34.1), Medium (API°=30.2), and Heavy (API°=27.4). The experimental setup is shown in FIG. 1.

FIG. 1 is a block diagram showing an example of an experimental setup 100, according to some implementations of the present disclosure. During the experiment, the crude oil sample 102 was placed in a sample holder, in this example, a standard commercial quartz cuvette having a square-base and 10 millimeter (mm) optical path length. The crude oil sample 102 was excited by a pulsed UV laser beam 106 of wavelength 266 nanometers (nm) and energy of approximately 15 millijoules (mJ) per pulse. The excitation was done at two different angles-of-incidence 108a and 108b (10° and 40°, respectively) relative to a perpendicular 110 to the surface of the cuvette. In general, the first angle-of-incidence can be in a range from 5° to 30°, and the second angle-of-incidence can be in a range from 30° to 70°. The resulting fluorescence 112 was collected by a quartz lens 114 which was then focused onto a Charge Coupled Device (CCD) spectrometer 116, with some filtering occurring. For example, a filter 118 positioned between the surface and the detector can be configured to pass a specified range of wavelengths and filter out wavelengths different from a pre-determined range. A fiber optic cable can be positioned between the lens 114 and the CCD spectrometer 116 (serving as a detector). The fiber optic cable can have an inlet configured to receive the focused fluorescence emission and an outlet positioned to direct the focused fluorescence emission to the CCD spectrometer 116. For each of the two laser angles-of-incidence, the spectrometer was scanned in the 280-650 nm range. Recorded data 120 was recorded in a personal computer as intensity versus wavelength arrays $I(\lambda)$ from which further data analysis occurred.

Data analysis includes normalizing the intensity of the recorded spectra so that their intensity at a chosen wavelength is made equal to 1, that is IN ($\lambda$), subtracting the 40° spectrum from the 10° spectrum to produce $\Delta IN$ ($\lambda$), and calculating the area under the curve in a specific range. During experimentation, the intensity at which the normalization was made was 420 nm, which is near the maximum of the fluorescence spectrum for petroleum crude oils. The specific range in which the areas under the curve were calculated was from 280 nm to 420 nm.

The calculated areas-under-the-curve were then correlated to the API gravity values, which gave rise to a straight line fit with R2 value of 0.997. The fluorescence spectra that were measured under the above conditions for the Extra Light, Light, Medium, and Heavy crude oils are shown in FIGS. 2-5, respectively.

The experimental setup 100 also depicts a fluorescence-measurement apparatus that includes the following components. A single-wavelength light source, such as the laser beams 106, is configured to generate an excitation light source. A sample holder 104, for example, a standard commercial quartz cuvette 104, defines an inner cavity configured to hold a sample and including a surface transparent to the excitation light source. One or more mounts, for example, can be attached to at least one of the single-wavelength light source (for example, to hold the laser beams 106) or the sample holder. The one or more mounts can be configured to change an incident angle of the excitation light source on the surface. One or more optical components, for example, the lens 114, can be positioned in a path of a fluorescence emission emitted from the surface. The one or more optical components can be configured to guide the fluorescence emission to a detector configured to obtain spectra from at least a first angle-of-incidence and a second angle-of-incidence. A recording/analyzing device, for example the personal computer that receives the recorded data 120, can perform the following functions. Spectra obtained by the detector from the first angle-of-incidence and the second angle-of-incidence can be recorded. Intensities of the spectra can be normalized and analyzed. A first spectrum corresponding to the first angle-of-incidence to obtain a difference in the spectra. A sample type of the sample can be identified based on an API gravity that is mapped to the difference.

Figure 2:
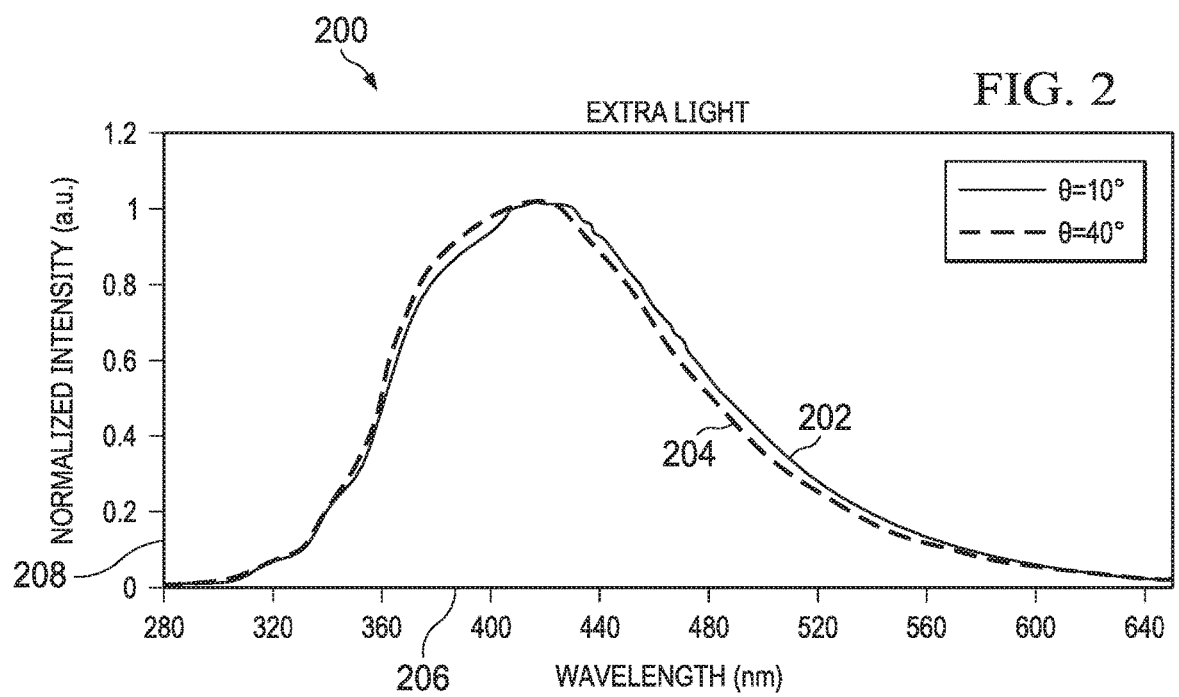
FIG. 2 is a graph showing an example of laser-induced fluorescence spectra for Extra Light crude oil, according to some implementations of the present disclosure.

FIG. 2 is a graph 200 showing an example of laser-induced fluorescence spectra 202 and 204 for Extra Light crude oil, according to some implementations of the present disclosure. For example, the Laser-induced fluorescence spectra is excited with a wavelength of 266 nm at two different laser angles-of-incidence of 10° and 40°, respectively. The intensities of both spectra have been normalized to unity at 420 nm. The intensities are plotted relative to wavelength axis 206 (in nm) and a normalized intensity 208, in arbitrary units (a.u.).

Figure 3:
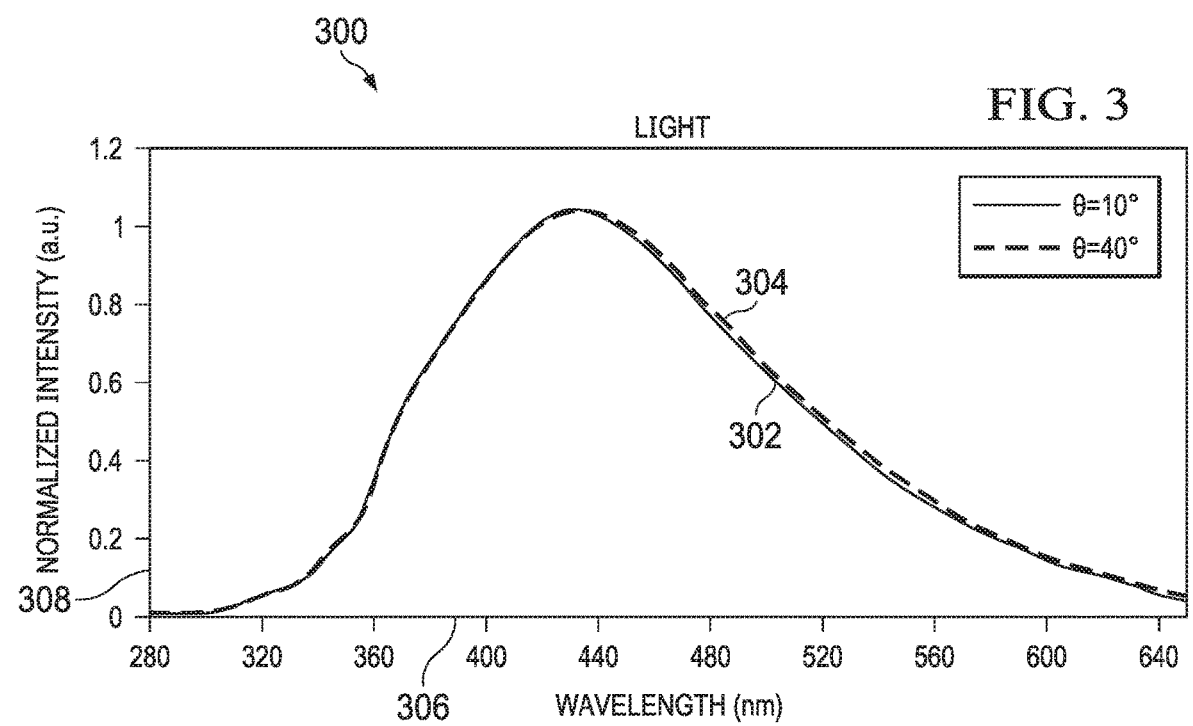
FIG. 3 is a graph showing an example of Laser-induced fluorescence spectra for Light crude oil, according to some implementations of the present disclosure.

FIG. 3 is a graph 300 showing an example of Laser-induced fluorescence spectra 302 and 304 for Light crude oil, according to some implementations of the present disclosure. For example, the Light crude oil is excited with a wavelength of 266 nm at two different laser angles-of-incidence of 10° and 40°, respectively. The intensities of both spectra have been normalized to unity at 420 nm. The intensities are plotted relative to wavelength axis 306 (in nm) and a normalized intensity 308 (in a.u.).

Figure 4:
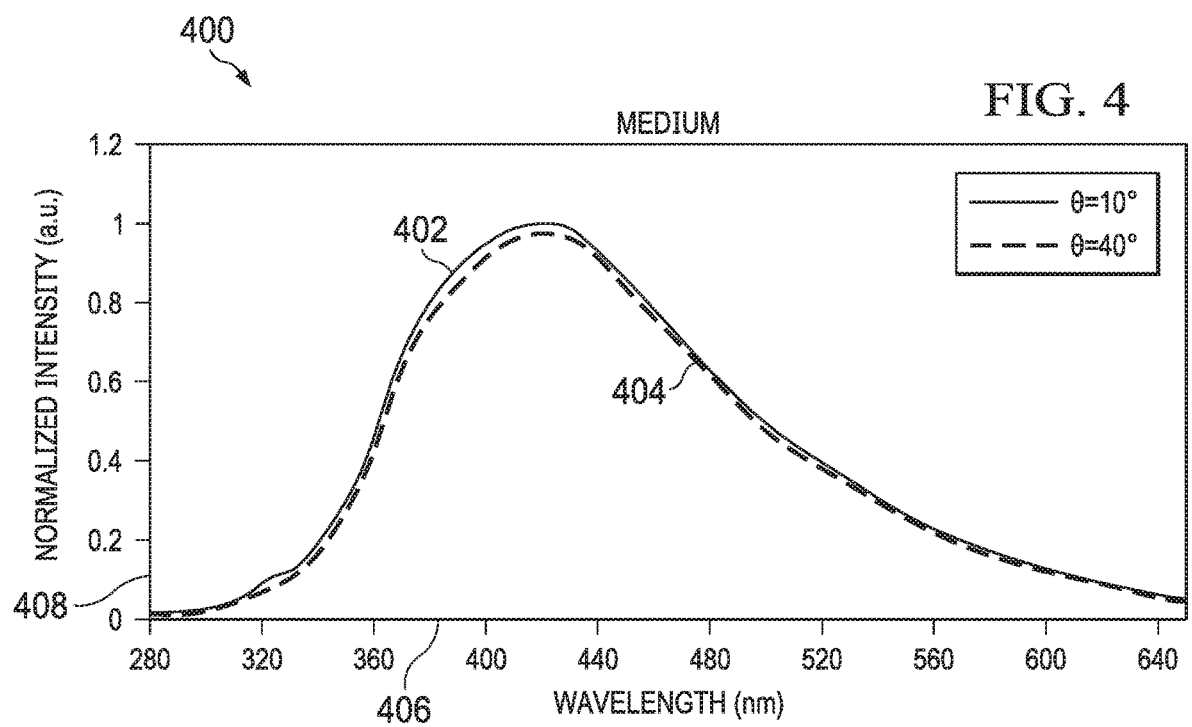
FIG. 4 is a graph showing an example of Laser-induced fluorescence spectra for Medium crude oil, according to some implementations of the present disclosure.

FIG. 4 is a graph 400 showing an example of Laser-induced fluorescence spectra 402 and 404 for Medium crude oil, according to some implementations of the present disclosure. For example, the Medium crude oil is excited with a wavelength of 266 nm at two different laser angles-of-incidence of 10° and 40°, respectively. The intensities of both spectra have been normalized to unity at 420 nm. The intensities are plotted relative to wavelength axis 406 (in nm) and a normalized intensity 408 (in a.u.).

Figure 5:
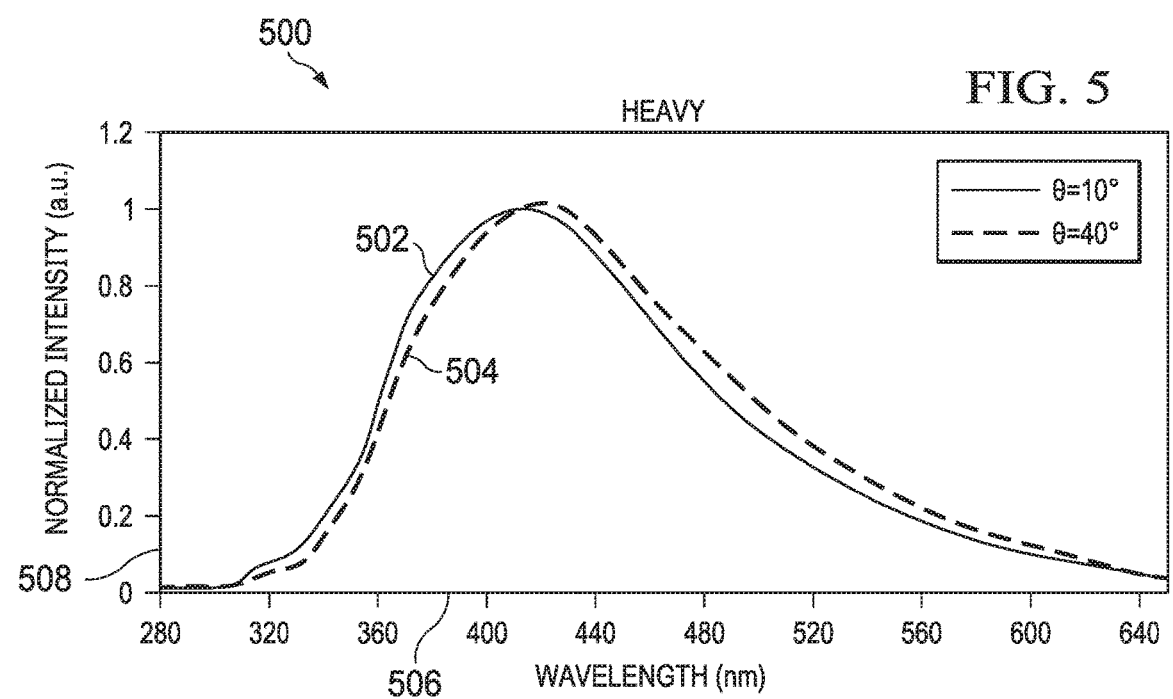
FIG. 5 is a graph showing an example of Laser-induced fluorescence spectra for the Heavy crude oil, according to some implementations of the present disclosure.
Figure 6A:
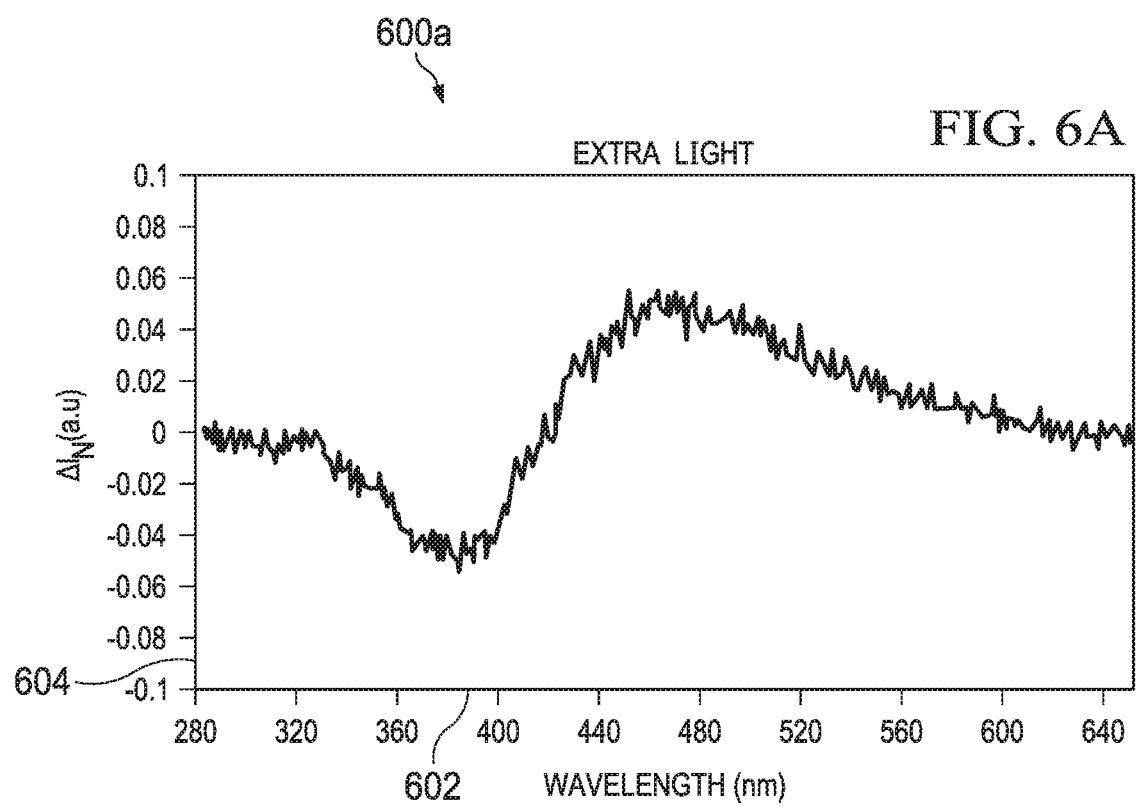
FIGS. 6A-6D are graphs showing examples of plots of intensity differences between the two spectra as functions of wavelength for each crude oil, according to some implementations of the present disclosure.
Figure 6B:
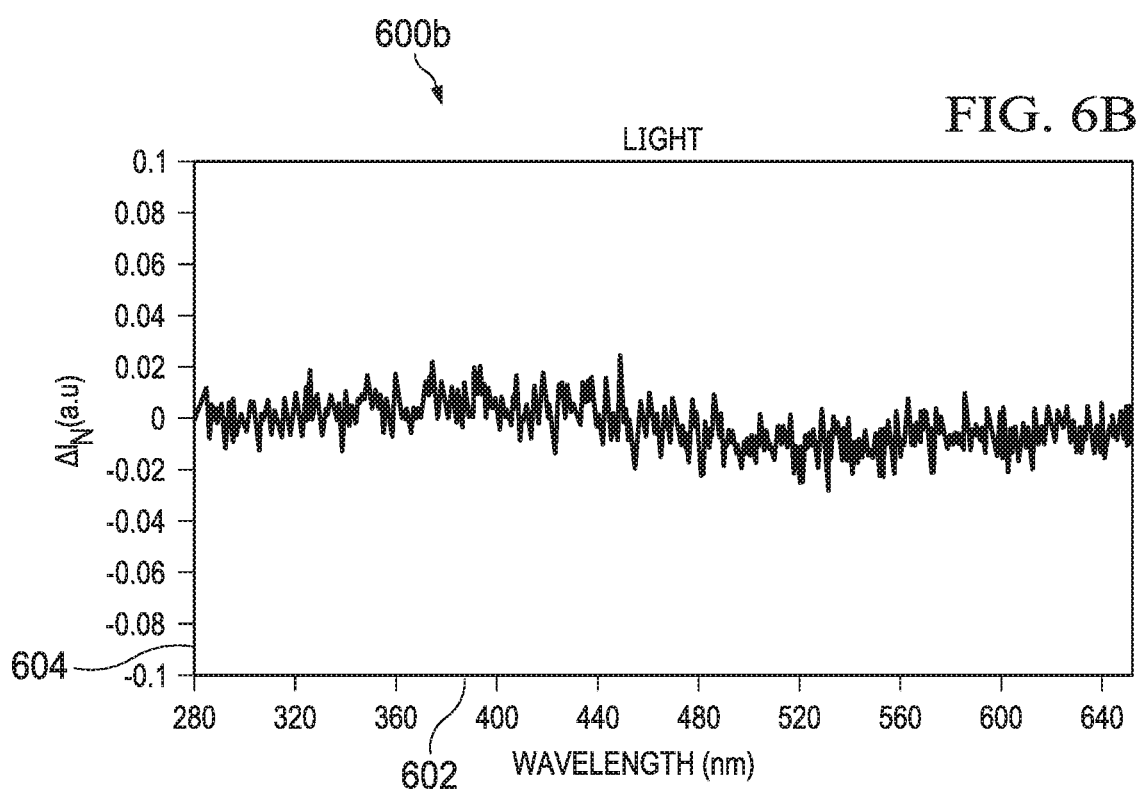
Figure 6C:
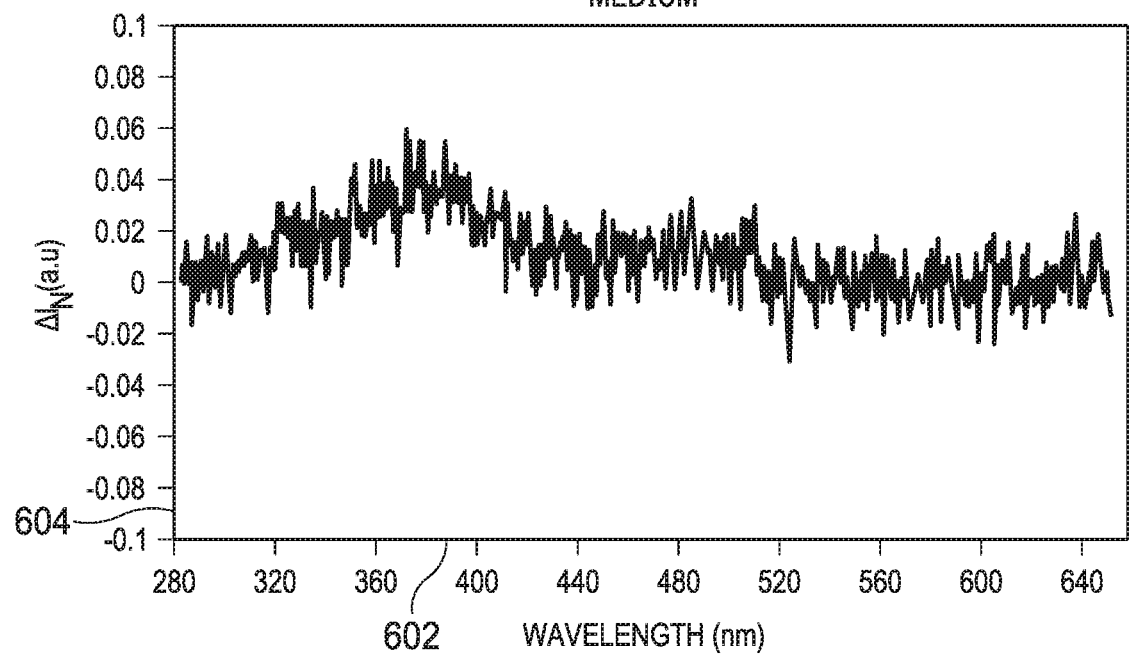
Figure 6D:
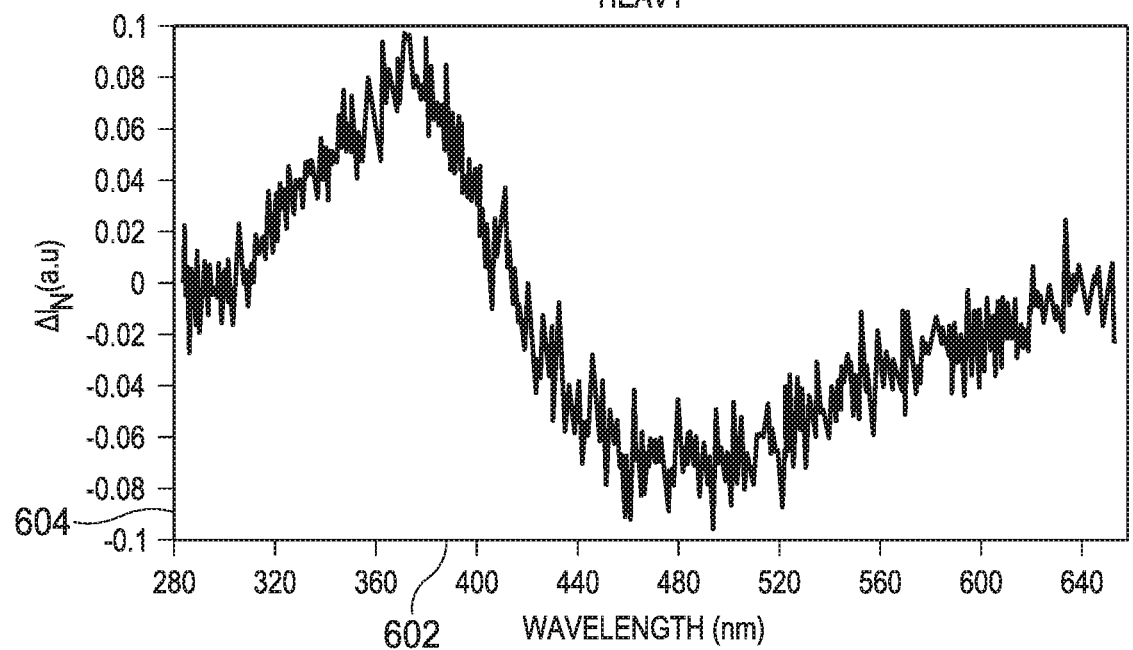

FIG. 5 is a graph 500 showing an example of Laser-induced fluorescence spectra 502 and 504 for the Heavy crude oil, according to some implementations of the present disclosure. For example, the Heavy crude oil is excited with a wavelength of 266 nm at two different laser angles-of-incidence of 10° and 40°, respectively. The intensities of both spectra have been normalized to unity at 420 nm. The intensities are plotted relative to wavelength axis 506 (in nm) and a normalized intensity 508 (in a.u.).

FIGS. 6A-6D are graphs showing examples of plots 600a-600d of intensity 604 differences between the two spectra as functions of wavelength 602 for each crude oil, according to some implementations of the present disclosure. For example, FIGS. 6A-6D show spectral subtraction plots between the normalized fluorescence spectra measured at 10° and those measured at 40° for the 4 different crude oils. The plots exhibit a systematic change in the shape with the API gravity of the crude oil. As the API gravity decreases, the segment below the 420 nm (the wavelength at which the intensity is normalized) increases its value, while the segment above the 420 nm decreases its value.

Figure 7:
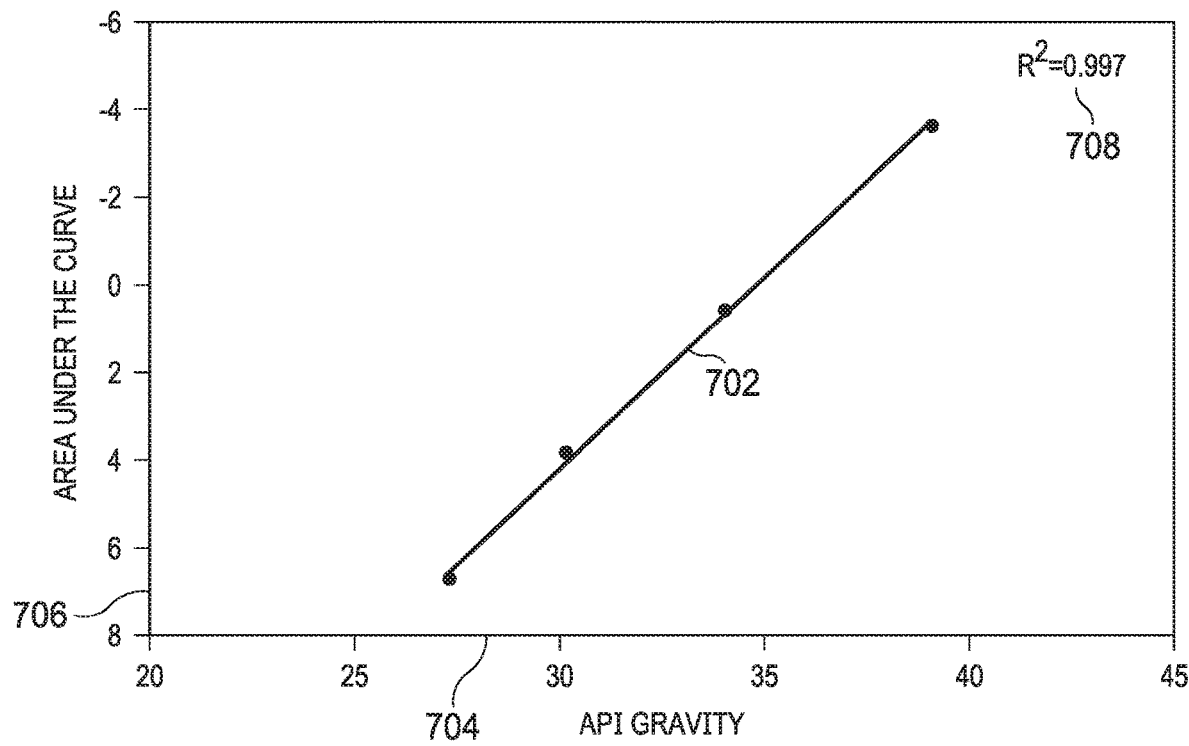
FIG. 7 is a graph showing an example of a plot of areas-under-the-curves in the spectral subtraction graphs of FIGS. 6A-6D as function of American Petroleum Institute (API) gravity, according to some implementations of the present disclosure.

FIG. 7 is a graph 700 showing an example of a plot 702 of areas-under-the-curves 706 in the spectral subtraction graphs of FIGS. 6A-6D as function of API gravity 704, according to some implementations of the present disclosure. By calculating the areas-under-the-curves between 280 nm and 420 nm and correlating areas-under-the-curves to the API gravity values of the crude oils, an excellent straight line fit 708 (for example, $R^2$=0.997) is achieved. This straight line can be used as a calibration line from which the API value of the crude oils can be calculated using techniques described in the present disclosure.

Figure 8:
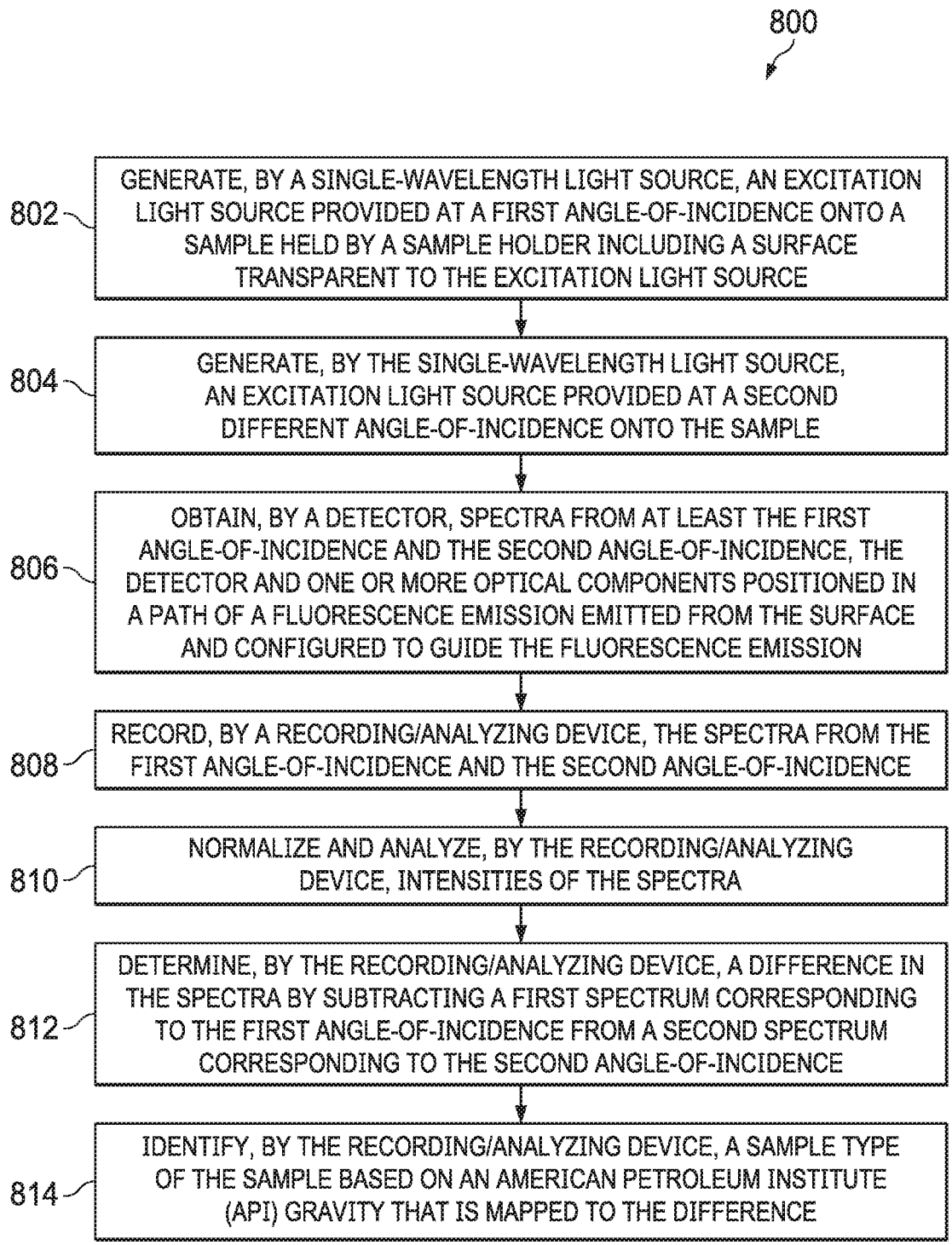
FIG. 8 is a flowchart of an example of a method for using a different in laser-induced fluorescence spectra to identify an API gravity of the crude oil, according to some implementations of the present disclosure.

FIG. 8 is a flowchart of an example of a method 800 for using a different in laser-induced fluorescence spectra to identify an API gravity of the crude oil, according to some implementations of the present disclosure. For clarity of presentation, the description that follows generally describes method 800 in the context of the other figures in this description. However, it will be understood that method 800 can be performed, for example, by any suitable system, environment, software, and hardware, or a combination of systems, environments, software, and hardware, as appropriate. In some implementations, various steps of method 800 can be run in parallel, in combination, in loops, or in any order.

At 802, an excitation light source is generating by a single-wavelength light source and is provided at a first angle-of-incidence onto a sample held by a sample holder including a surface transparent to the excitation light source. The sample holder can be configured to expose the sample in relation to the excitation light source. In some implementations, the excitation light source can emits a beam of light containing multiple wavelengths with at least one wavelength that is capable of generating fluorescence in the sample. In some implementations, the light source can be a laser that emits a laser beam at a defined wavelength, for example, in an ultraviolet wavelength. As an example, the wavelength of a light beam can be between 266 nm and 355 nm. The light source can have a power output between twenty and fifty milliwatts, for example. In some implementations, the sample can fluoresce after one second of exposure to the light beam. The light source can emit either a continuous or pulsed light beam. From 802, method 800 proceeds to 804.

At 804, an excitation light source is generated by the single-wavelength light source and is provided at a second different angle-of-incidence onto the sample. For example, the single-wavelength light source can be the same type of source used as the first angle-of-incidence. From 804, method 800 proceeds to 806.

At 806, spectra from at least the first angle-of-incidence and the second angle-of-incidence are obtained by a detector. For example, the detector and one or more optical components can be positioned in a path of a fluorescence emission emitted from the surface and configured to guide the fluorescence emission. From 806, method 800 proceeds to 808.

At 808, the spectra from the first angle-of-incidence and the second angle-of-incidence recorded by a recording/analyzing device. For example, the CCD spectrometer 116 can capture the spectra, as indicated in FIG. 1, and provide the recorded data 120 for recording in a personal computer. From 808, method 800 proceeds to 810.

At 810, intensities of the spectra are normalized and analyzed by the recording/analyzing device. The intensities that are normalized and analyzed can correspond to the separate plots shown in the graphs of FIGS. 2-5, for example. From 810, method 800 proceeds to 812.

At 812, a difference in the spectra is determined by the recording/analyzing device by subtracting a first spectrum corresponding to the first angle-of-incidence from a second spectrum corresponding to the second angle-of-incidence. The differences can correspond to differences between the separate plots shown in the graphs of FIGS. 2-5, for example. From 812, method 800 proceeds to 814.

At 814, a sample type of the sample is identified by the recording/analyzing device based on an API gravity that is mapped to the difference. For example, the recording/analyzing device can determine that the sample is a hydrocarbon fluid, and that the API gravity of the sample indicates that the sample is one of Extra Light, Light, Medium, and Heavy crude oil. The identification can also indicate that the sample falls between two types, such as somewhere between Extra Light and Light. After 814, method 800 can stop.

Figure 9:
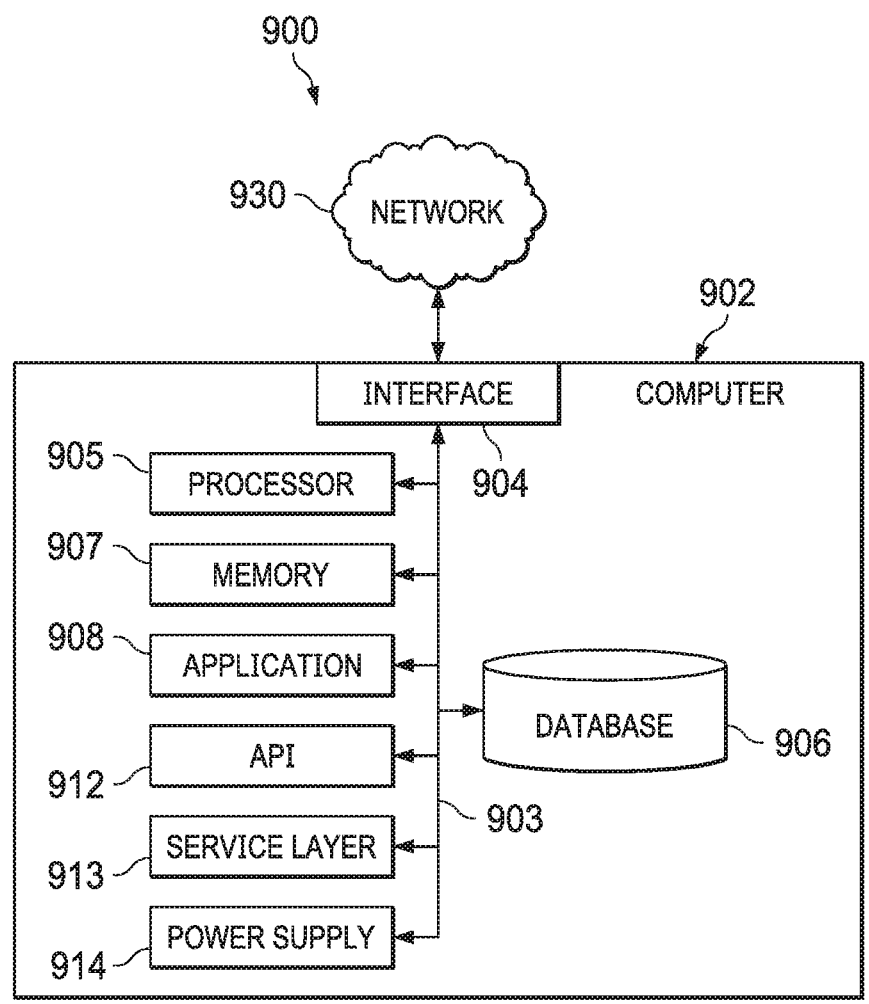
FIG. 9 is a block diagram illustrating an example computer system used to provide computational functionalities associated with described algorithms, methods, functions, processes, flows, and procedures as described in the present disclosure, according to some implementations of the present disclosure.

FIG. 9 is a block diagram of an example computer system 900 used to provide computational functionalities associated with described algorithms, methods, functions, processes, flows, and procedures described in the present disclosure, according to some implementations of the present disclosure. The illustrated computer 902 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 902 can include input devices such as keypads, keyboards, and touch screens that can accept user information. Also, the computer 902 can include output devices that can convey information associated with the operation of the computer 902. The information can include digital data, visual data, audio information, or a combination of information. The information can be presented in a graphical user interface (UI) (or GUI).

The computer 902 can serve in a role as a client, a network component, a server, a database, a persistency, or components of a computer system for performing the subject matter described in the present disclosure. The illustrated computer 902 is communicably coupled with a network 930. In some implementations, one or more components of the computer 902 can be configured to operate within different environments, including cloud-computing-based environments, local environments, global environments, and combinations of environments.

At a top level, the computer 902 is an electronic computing device operable to receive, transmit, process, store, and manage data and information associated with the described subject matter. According to some implementations, the computer 902 can also include, or be communicably coupled with, an application server, an email server, a web server, a caching server, a streaming data server, or a combination of servers.

The computer 902 can receive requests over network 930 from a client application (for example, executing on another computer 902). The computer 902 can respond to the received requests by processing the received requests using software applications. Requests can also be sent to the computer 902 from internal users (for example, from a command console), external (or third) parties, automated applications, entities, individuals, systems, and computers.

Each of the components of the computer 902 can communicate using a system bus 903. In some implementations, any or all of the components of the computer 902, including hardware or software components, can interface with each other or the interface 904 (or a combination of both) over the system bus 903. Interfaces can use an application programming interface (API) 912, a service layer 913, or a combination of the API 912 and service layer 913. The API 912 can include specifications for routines, data structures, and object classes. The API 912 can be either computer-language independent or dependent. The API 912 can refer to a complete interface, a single function, or a set of APIs.

The service layer 913 can provide software services to the computer 902 and other components (whether illustrated or not) that are communicably coupled to the computer 902. The functionality of the computer 902 can be accessible for all service consumers using this service layer. Software services, such as those provided by the service layer 913, can provide reusable, defined functionalities through a defined interface. For example, the interface can be software written in JAVA, C++, or a language providing data in extensible markup language (XML) format. While illustrated as an integrated component of the computer 902, in alternative implementations, the API 912 or the service layer 913 can be stand-alone components in relation to other components of the computer 902 and other components communicably coupled to the computer 902. Moreover, any or all parts of the API 912 or the service layer 913 can be implemented as child or sub-modules of another software module, enterprise application, or hardware module without departing from the scope of the present disclosure.

The computer 902 includes an interface 904. Although illustrated as a single interface 904 in FIG. 9, two or more interfaces 904 can be used according to particular needs, desires, or particular implementations of the computer 902 and the described functionality. The interface 904 can be used by the computer 902 for communicating with other systems that are connected to the network 930 (whether illustrated or not) in a distributed environment. Generally, the interface 904 can include, or be implemented using, logic encoded in software or hardware (or a combination of software and hardware) operable to communicate with the network 930. More specifically, the interface 904 can include software supporting one or more communication protocols associated with communications. As such, the network 930 or the interface's hardware can be operable to communicate physical signals within and outside of the illustrated computer 902.

The computer 902 includes a processor 905. Although illustrated as a single processor 905 in FIG. 9, two or more processors 905 can be used according to particular needs, desires, or particular implementations of the computer 902 and the described functionality. Generally, the processor 905 can execute instructions and can manipulate data to perform the operations of the computer 902, including operations using algorithms, methods, functions, processes, flows, and procedures as described in the present disclosure.

The computer 902 also includes a database 906 that can hold data for the computer 902 and other components connected to the network 930 (whether illustrated or not). For example, database 906 can be an in-memory, conventional, or a database storing data consistent with the present disclosure. In some implementations, database 906 can be a combination of two or more different database types (for example, hybrid in-memory and conventional databases) according to particular needs, desires, or particular implementations of the computer 902 and the described functionality. Although illustrated as a single database 906 in FIG. 9, two or more databases (of the same, different, or combination of types) can be used according to particular needs, desires, or particular implementations of the computer 902 and the described functionality. While database 906 is illustrated as an internal component of the computer 902, in alternative implementations, database 906 can be external to the computer 902.

The computer 902 also includes a memory 907 that can hold data for the computer 902 or a combination of components connected to the network 930 (whether illustrated or not). Memory 907 can store any data consistent with the present disclosure. In some implementations, memory 907 can be a combination of two or more different types of memory (for example, a combination of semiconductor and magnetic storage) according to particular needs, desires, or particular implementations of the computer 902 and the described functionality. Although illustrated as a single memory 907 in FIG. 9, two or more memories 907 (of the same, different, or combination of types) can be used according to particular needs, desires, or particular implementations of the computer 902 and the described functionality. While memory 907 is illustrated as an internal component of the computer 902, in alternative implementations, memory 907 can be external to the computer 902.

The application 908 can be an algorithmic software engine providing functionality according to particular needs, desires, or particular implementations of the computer 902 and the described functionality. For example, application 908 can serve as one or more components, modules, or applications. Further, although illustrated as a single application 908, the application 908 can be implemented as multiple applications 908 on the computer 902. In addition, although illustrated as internal to the computer 902, in alternative implementations, the application 908 can be external to the computer 902.

The computer 902 can also include a power supply 914. The power supply 914 can include a rechargeable or non-rechargeable battery that can be configured to be either user- or non-user-replaceable. In some implementations, the power supply 914 can include power-conversion and management circuits, including recharging, standby, and power management functionalities. In some implementations, the power-supply 914 can include a power plug to allow the computer 902 to be plugged into a wall socket or a power source to, for example, power the computer 902 or recharge a rechargeable battery.

There can be any number of computers 902 associated with, or external to, a computer system containing computer 902, with each computer 902 communicating over network 930. Further, the terms "client," "user," and other appropriate terminology can be used interchangeably, as appropriate, without departing from the scope of the present disclosure. Moreover, the present disclosure contemplates that many users can use one computer 902 and one user can use multiple computers 902.

Described implementations of the subject matter can include one or more features, alone or in combination.

In a first implementation, a fluorescence-measurement apparatus includes the following. A single-wavelength light source is configured to generate an excitation light source. A sample holder defining an inner cavity is configured to hold a sample and includes a surface transparent to the excitation light source. One or more mounts attached to at least one of the single-wavelength light source or the sample holder is configured to change an incident angle of the excitation light source on the surface. One or more optical components positioned in a path of a fluorescence emission emitted from the surface is configured to guide the fluorescence emission to a detector configured to obtain spectra from at least a first angle-of-incidence and a second angle-of-incidence. A recording/analyzing device is configured to: record spectra obtained by the detector from the first angle-of-incidence and the second angle-of-incidence, normalize and analyze intensities of the spectra, subtract a first spectrum corresponding to the first angle-of-incidence from a second spectrum corresponding to the second angle-of-incidence to obtain a difference in the spectra, and identify a sample type of the sample based on an American Petroleum Institute (API) gravity that is mapped to the difference.

The foregoing and other described implementations can each, optionally, include one or more of the following features:

A first feature, combinable with any of the following features, where the sample holder is configured to expose the sample in relation to the excitation light source.

A second feature, combinable with any of the previous or following features, where the first angle-of-incidence is in a range from 5° to 30°.

A third feature, combinable with any of the previous or following features, where the second angle-of-incidence is in a range from 30° to 70°.

A fourth feature, combinable with any of the previous or following features, where the excitation light source includes a laser in an ultraviolet spectrum at a defined wavelength.

A fifth feature, combinable with any of the previous or following features, the fluorescence-measurement apparatus further including a filter positioned between the surface and the detector and configured to pass a specified range of wavelengths and filter out wavelengths different from a pre-determined range.

A sixth feature, combinable with any of the previous or following features, where the one or more optical components include: a lens positioned between the surface and the detector and configured to focus the fluorescence emission onto a Charge Coupled Device (CCD) spectrometer; and a fiber optic cable positioned between the lens and the detector and having an inlet configured to receive the focused fluorescence emission and an outlet positioned to direct the focused fluorescence emission to the detector.

A seventh feature, combinable with any of the previous or following features, where the sample includes a hydrocarbon fluid, and where the API gravity corresponds to one of Extra Light, Light, Medium, and Heavy.

For example, in a second implementation, a computer-implemented method includes the following. An excitation light source is generated by a single-wavelength light source and is provided at a first angle-of-incidence onto a sample held by a sample holder including a surface transparent to the excitation light source. An excitation light source is generated by the single-wavelength light source and is provided at a second different angle-of-incidence onto the sample. Spectra from at least the first angle-of-incidence and the second angle-of-incidence are obtained by a detector. The detector and one or more optical components are positioned in a path of a fluorescence emission emitted from the surface and configured to guide the fluorescence emission. The spectra from the first angle-of-incidence and the second angle-of-incidence recorded by a recording/analyzing device. Intensities of the spectra are normalized and analyzed by the recording/analyzing device. A difference in the spectra is determined by the recording/analyzing device by subtracting a first spectrum corresponding to the first angle-of-incidence from a second spectrum corresponding to the second angle-of-incidence. A sample type of the sample is identified by the recording/analyzing device based on an American Petroleum Institute (API) gravity that is mapped to the difference.

The foregoing and other described implementations can each, optionally, include one or more of the following features:

A first feature, combinable with any of the following features, where the sample holder is configured to expose the sample in relation to the excitation light source.

A second feature, combinable with any of the previous or following features, where the first angle-of-incidence is in a range from 5° to 30°.

A third feature, combinable with any of the previous or following features, where the second angle-of-incidence is in a range from 30° to 70°.

A fourth feature, combinable with any of the previous or following features, where the excitation light source includes a laser in an ultraviolet spectrum at a defined wavelength.

A fifth feature, combinable with any of the previous or following features, the method further including filtering out a specified range of wavelengths in a pre-determined range.

A sixth feature, combinable with any of the previous or following features, where the one or more optical components include a lens positioned between the surface and the detector and configured to focus the fluorescence emission onto a CCD spectrometer and a fiber optic cable positioned between the lens and the detector and having an inlet configured to receive the focused fluorescence emission and an outlet positioned to direct the focused fluorescence emission to the detector.

A seventh feature, combinable with any of the previous or following features, where the sample includes a hydrocarbon fluid, and where the API gravity corresponds to one of Extra Light, Light, Medium, and Heavy.

In a third implementation, a non-transitory, computer-readable medium stores one or more instructions executable by a computer system to perform operations including the following. An excitation light source is generated by a single-wavelength light source and is provided at a first angle-of-incidence onto a sample held by a sample holder including a surface transparent to the excitation light source. An excitation light source is generated by the single-wavelength light source and is provided at a second different angle-of-incidence onto the sample. Spectra from at least the first angle-of-incidence and the second angle-of-incidence are obtained by a detector. The detector and one or more optical components are positioned in a path of a fluorescence emission emitted from the surface and configured to guide the fluorescence emission. The spectra from the first angle-of-incidence and the second angle-of-incidence recorded by a recording/analyzing device. Intensities of the spectra are normalized and analyzed by the recording/analyzing device. A difference in the spectra is determined by the recording/analyzing device by subtracting a first spectrum corresponding to the first angle-of-incidence from a second spectrum corresponding to the second angle-of-incidence. A sample type of the sample is identified by the recording/analyzing device based on an American Petroleum Institute (API) gravity that is mapped to the difference.

The foregoing and other described implementations can each, optionally, include one or more of the following features:

A first feature, combinable with any of the following features, where the sample holder is configured to expose the sample in relation to the excitation light source.

A second feature, combinable with any of the previous or following features, where the first angle-of-incidence is in a range from 5° to 30°.

A third feature, combinable with any of the previous or following features, where the second angle-of-incidence is in a range from 30° to 70°.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A fluorescence-measurement apparatus, comprising:
   a single-wavelength light source configured to generate an excitation light source;
   a sample holder defining an inner cavity configured to hold a sample and including a surface transparent to the excitation light source;
   one or more mounts attached to at least one of the single-wavelength light source or the sample holder and configured to change an incident angle of the excitation light source on the surface;
   one or more optical components positioned in a path of a fluorescence emission emitted from the surface and configured to guide the fluorescence emission to a detector configured to obtain spectra from at least a first angle-of-incidence and a second different angle-of-incidence; and
   a recording/analyzing device configured to:
      record spectra obtained by the detector from the first angle-of-incidence and the second different angle-of-incidence;
      normalize and analyze intensities of the spectra;
      subtract a first spectrum corresponding to the first angle-of-incidence from a second spectrum corresponding to the second different angle-of-incidence to obtain a difference in the spectra; and
      identify a sample type of the sample based on an American Petroleum Institute (API) gravity that is mapped to the difference.

2. The fluorescence-measurement apparatus of claim 1, wherein the sample holder is configured to expose the sample in relation to the excitation light source.

3. The fluorescence-measurement apparatus of claim 1, wherein the first angle-of-incidence is in a range from 5° to 30°.

4. The fluorescence-measurement apparatus of claim 1, wherein the second different angle-of-incidence is in a range from 30° to 70°.

5. The fluorescence-measurement apparatus of claim 1, wherein the excitation light source comprises a laser in an ultraviolet spectrum at a defined wavelength.

6. The fluorescence-measurement apparatus of claim 1, further comprising a filter positioned between the surface and the detector and configured to pass a specified range of wavelengths and filter out wavelengths different from a pre-determined range.

7. The fluorescence-measurement apparatus of claim 1, wherein the one or more optical components comprise:
   a lens positioned between the surface and the detector and configured to focus the fluorescence emission onto a Charge Coupled Device (CCD) spectrometer; and
   a fiber optic cable positioned between the lens and the detector and having an inlet configured to receive the focused fluorescence emission and an outlet positioned to direct the focused fluorescence emission to the detector.

8. The fluorescence-measurement apparatus of claim 1, wherein the sample comprises a hydrocarbon fluid, and wherein the API gravity corresponds to one of Extra Light, Light, Medium, and Heavy.

9. A computer-implemented method comprising:
   generating, by a single-wavelength light source, an excitation light source provided at a first angle-of-incidence onto a sample held by a sample holder including a surface transparent to the excitation light source;
   generating, by the single-wavelength light source, an excitation light source provided at a second different angle-of-incidence onto the sample;
   obtaining, by a detector, spectra from at least the first angle-of-incidence and the second different angle-of-incidence, the detector and one or more optical components positioned in a path of a fluorescence emission emitted from the surface and configured to guide the fluorescence emission;
   recording, by a recording/analyzing device, the spectra from the first angle-of-incidence and the second different angle-of-incidence;
   normalizing and analyzing, by the recording/analyzing device, intensities of the spectra;
   determining, by the recording/analyzing device, a difference in the spectra by subtracting a first spectrum corresponding to the first angle-of-incidence from a second spectrum corresponding to the second different angle-of-incidence; and identifying, by the recording/analyzing device, a sample type of the sample based on an American Petroleum Institute (API) gravity that is mapped to the difference.

10. The computer-implemented method of claim 9, wherein the sample holder is configured to expose the sample in relation to the excitation light source.

11. The computer-implemented method of claim 9, wherein the first angle-of-incidence is in a range from 5° to 30°.

12. The computer-implemented method of claim 9, wherein the second different angle-of-incidence is in a range from 30° to 70°.

13. The computer-implemented method of claim 9, wherein the excitation light source comprises a laser in an ultraviolet spectrum at a defined wavelength.

14. The computer-implemented method of claim 9, further comprising:
filtering out a specified range of wavelengths in a predetermined range.

15. The computer-implemented method of claim 9, wherein the one or more optical components comprise:
a lens positioned between the surface and the detector and configured to focus the fluorescence emission onto a CCD spectrometer; and
a fiber optic cable positioned between the lens and the detector and having an inlet configured to receive the focused fluorescence emission and an outlet positioned to direct the focused fluorescence emission to the detector.

16. The computer-implemented method of claim 9, wherein the sample comprises a hydrocarbon fluid, and wherein the API gravity corresponds to one of Extra Light, Light, Medium, and Heavy.

17. A non-transitory, computer-readable medium storing one or more instructions executable by a computer system to perform operations comprising:

generating, by a single-wavelength light source, an excitation light source provided at a first angle-of-incidence onto a sample held by a sample holder including a surface transparent to the excitation light source;

generating, by the single-wavelength light source, an excitation light source provided at a second different angle-of-incidence onto the sample;

obtaining, by a detector, spectra from at least the first angle-of-incidence and the second different angle-of-incidence, the detector and one or more optical components positioned in a path of a fluorescence emission emitted from the surface and configured to guide the fluorescence emission;

recording, by a recording/analyzing device, the spectra from the first angle-of-incidence and the second different angle-of-incidence;

normalizing and analyzing, by the recording/analyzing device, intensities of the spectra;

determining, by the recording/analyzing device, a difference in the spectra by subtracting a first spectrum corresponding to the first angle-of-incidence from a second spectrum corresponding to the second different angle-of-incidence; and identifying, by the recording/analyzing device, a sample type of the sample based on an American Petroleum Institute (API) gravity that is mapped to the difference.

18. The non-transitory, computer-readable medium of claim 17, wherein the sample holder is configured to expose the sample in relation to the excitation light source.

19. The non-transitory, computer-readable medium of claim 17, wherein the first angle-of-incidence is in a range from 5° to 30°.

20. The non-transitory, computer-readable medium of claim 17, wherein the second different angle-of-incidence is in a range from 30° to 70°.

* * * * *